United States Patent [19]

Ito

[11] 4,084,541
[45] Apr. 18, 1978

[54] DYEING AND DECOLORIZATION APPARATUS FOR USE IN A BLOOD SERUM ANALYZER OF AN ELECTROPHORETIC TYPE

[75] Inventor: Hiromi Ito, Hachiouji, Japan

[73] Assignee: Olympus Optical Co., Ltd., Japan

[21] Appl. No.: 678,712

[22] Filed: Apr. 20, 1976

[30] Foreign Application Priority Data

| Apr. 22, 1975 | Japan | 50-48135 |
| Dec. 8, 1975 | Japan | 50-146168 |
| Jan. 17, 1976 | Japan | 51-4512 |
| Jan. 17, 1976 | Japan | 51-4513 |

[51] Int. Cl.² ............................................. B05C 3/00
[52] U.S. Cl. ........................................ 118/421; 118/7; 118/9; 118/506; 8/3; 23/230 B; 204/180 S; 427/2; 427/4
[58] Field of Search ............... 118/421, 419, 423, 249, 118/258, 259, 7, 506, 9; 68/171; 134/58 R, 134; 204/180 S, 180 G; 424/3; 427/2, 4; 8/3; 23/230 B

[56] References Cited

U.S. PATENT DOCUMENTS

| 3,093,051 | 6/1963 | Ritzerfeld et al. | 118/421 X |
| 3,133,009 | 5/1964 | Natelson | 204/180 S |
| 3,507,292 | 4/1970 | Pedersen | 118/423 X |
| 3,566,891 | 3/1971 | Koch | 118/421 X |
| 3,674,040 | 7/1972 | Howells et al. | 118/421 X |
| 3,688,735 | 9/1972 | Brenner | 118/9 |
| 3,848,439 | 11/1974 | Lopata | 118/421 X |
| 3,857,778 | 12/1974 | Hiratsuka et al. | 204/180 S |
| 3,871,895 | 3/1975 | Adler | 424/3 X |
| 3,964,434 | 6/1976 | Adler et al. | 118/506 X |
| 3,995,022 | 11/1976 | Heanley et al. | 118/506 X |
| 3,999,505 | 12/1976 | Kato et al. | 118/7 |

Primary Examiner—James Kee Chi
Attorney, Agent, or Firm—Cushman, Darby & Cushman

[57] ABSTRACT

An apparatus for dyeing and decolorizing a specimen carrier of, for example, paper film carrying a plurality of specimens such as blood serum to be analyzed which have been treated by means of an electrophoretic apparatus, comprising a mechanism for transporting and holding the specimen carrier, a dyeing trough containing a dyeing liquid agent, a decolorization trough containing a decolorization liquid agent, and a trough drive mechanism for successively moving the dyeing and decolorization troughs, whereby the troughs are respectively moved with respect to the specimen carrier held by the transporting and holding mechanism up to the position where the specimen carrier is dipped into the liquid agent.

10 Claims, 6 Drawing Figures

DYEING AND DECOLORIZATION APPARATUS FOR USE IN A BLOOD SERUM ANALYZER OF AN ELECTROPHORETIC TYPE

BACKGROUND OF THE INVENTION a. Field of the Invention:

The present invention generally relates to a dyeing and decolorization apparatus for use in a blood serum analyzer of elctrophoretic type, and more particularly to such apparatus for dyeing and decolorizing a specimen carrier of a belt-like paper carrying a plurality of different blood serums as specimens to be analyzed which have been treated by means of an electrophoretic apparatus in the analyzer.

b. Description of the prior art:

In an electrophoretic method for analyzing a blood serum i.e. for measuring quantities of different types of proteins in the blood serum, the blood serum as a specimen is applied first to a specimen carrier which consists of, for example, a cellulose acetate paper of belt-like form and the blood serum is fractionated into different components of proteins by means of electrophoresis by applying high direct voltage to the blood serum within a electrophoretic apparatus. Then the fractionated components of proteins are quantatively measured by a densitometer or filter photoelectric colorimeter. In this case in order to obtain the colored specimen clearly distinguishable on the specimen carrier of substantially clear for accurate densitometric measurements, the blood serum is colorized together with the specimen carrier by a colorization liquid agent and the colored specimen carrier is then thoroughly decolorized or clearized except for the portion of a decolorization liquid agent.

In the prior art, all of the process steps including dyeing and decolorization steps in the electrophoretic method for analyzing a blood serum are manually done by an expert and this is very inefficient in all its aspects. From the reason described above, so much efforts have been directed recently to realize an automated blood serum analyzer of electrophoretic type, in which all of the necessary process steps in the electrophoretic method are automatically performed. When automating the blood serum analyzer, the dyeing and decolorization steps among other process steps may be realized by using a suitable transport mechanism capable of transporting the specimen carrier which has been treated in the electrophoretic apparatus into the dyeing liquid agent contained in a dyeing trough, into the decolorization liquid agent in a decolorization trough and to the place where successive process step should be performed. Therefore, it is necessary in this case to dispose the carrier transport mechanism into the liquid agents in order to transport the specimen carrier under the liquid agents. However, smooth transportation of the specimen carrier under the liquid agent is almost impossible due to the fact that the specimen carrier used for the purpose of blood serum analysis is yielding in the liquid agent under the influence of the excess liquid resistance when the specimen carrier is transported under the liquid agents.

SUMMARY OF THE INVENTION

It is therefore a primary object of the present invention to provide a dyeing and decolorization apparatus for use in a blood serum analyzer of electrophoretic type, in which a dyeing trough containing a dyeing liquid agent and a decolorization trough containing a decolorization liquid agent are moved successively with respect to a carrier transport mechanism for transporting and holding a specimen carrier up to the position where the specimen carrier held by the carrier transport mechanism is dipped into each liquid agent.

It is another object of the present invention to provide a dyeing and decolorization apparatus for use in a blood serum analyzer of electrophoretic type, which is capable of performing needed dyeing and decolorization functions with high reliabilities.

BRIEF DESCRIPTION OF THE DRAWINGS

Other objects and features of the invention will become apparent to those skilled in the art as the disclosure made in the following description of preferred embodiments of the invention, as illustrated in the accompanying sheet of drawings, in which like reference characters designate the same parts throughout the figures and wherein.

DETAILED DESCRIPTION OF THE PREFERRED EMBODIMENTS

Figure 1:
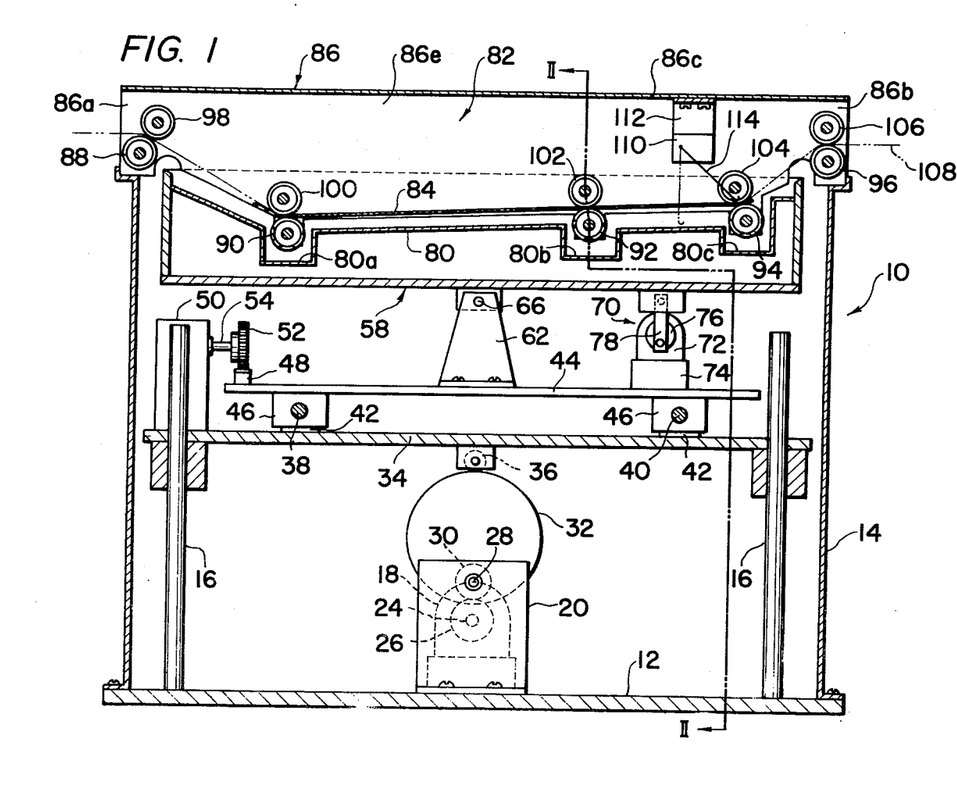
FIG. 1 shows a sectional side elevational view of a dyeing and decolorization apparatus embodying the present invention with some of parts or members removed for the purpose of clarity of the drawing.
Figure 2:
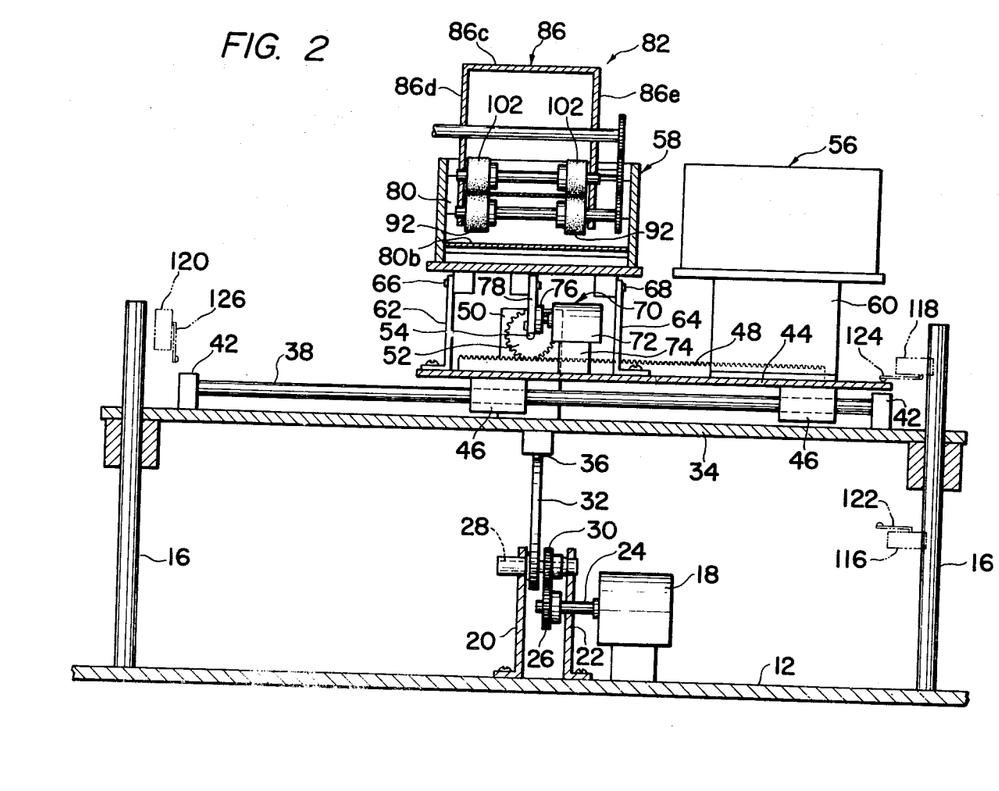
FIG. 2 shows a sectional front elevation view of the dyeing and decolorization apparatus as seen from the right along the line II—II of FIG. 1 with some of parts removed and some shown in phantom.

Referring now to FIGS. 1 and 2, there is shown a dyeing and decolorization apparatus 10 according to the present invention. The dyeing and decolorization apparatus 10 includes a base board 12 of a generally rectangular shape, to which a casing 14 and four guide posts 16 are fixed uprightly. A first electric motor 18 and a pair of supporting plates 20 and 22 are also fixed on the base board 12 at the central portion thereof. The pair of the supporting plates 20 and 22 are arranged in parallel with each other so that they define a space therebetween. A drive shaft 24 of the motor 18 extends through one supporting plate 22 and into the space between the plates 20 and 22. A gear 26 is fixed at the end portion of the drive shaft of the motor 18. A rotary shaft 28 is rotatably supported by the supporting plates 20 and 22 so that a gear 30 fixed to the shaft 28 can be in meshing engagement with the gear 26. A disk 32 is eccentrically fixed to the rotary shaft 28 at the portion between the supporting plates 20 and 22. Thus the eccentric disk 32 is rotated together with the rotary shaft 28 through the gears 30 and 26 when the motor 18 is rotated. A vertically movable plate 34 is slidably mounted to the four guide posts 16 so that it can move upwardly and downwardly along the guide posts 16. A small roller 36 as a follower is mounted to the bottom surface of the vertically movable plate 34 at the position where its periphery can engage with the peripheral surface of the eccentric disk 32. In FIGS. 1 and 2, the vertically movable plate 34 is supported in its uppermost position by the eccentric disk 32. However, since the uppermost portion of the periphery of the eccentric disk 32 is diplaced downwardly with the rotation thereof, the vertically movable plate 34 will move downwardly to its lowermost position by the gravity when the eccentric disk is rotated by the motor 18. Then the vertically movable plate 34 is gradually pushed up by the eccentric disk 32 to its uppermost position shown in FIGS. 1 and 2, since the uppermost portion of the periphery of the eccentric disk 32 is moved upwardly with the successive rotation of the disk 32.

A pair of guide rods 38 and 40 are disposed above the vertically movable plate 34 in parallel with each other and with the plate 34 with their both ends fixed to two pairs of support members 42 which are fixedly mounted on the plate 34. A horizontally movable plate 44 is slidably mounted on the guide rods 38 and 40 through four sliders 46 which are respectively fixed to the bottom surface of the plate 44. In order to move the plate 44 in horizontal directions i.e. in the right and left in FIG. 2, a rack 48 is fixedly mounted on the plate 44 so as to be parallel with the guide rods 38 and 40 and a second electric motor 50 is secured to the vertically movable plate 34 so that a pinion 52 fixed to a motor drive shaft 54 can be in meshing engagement with the rack 48. Therefore, the horizontally movable plate 44 is moved from the rightmost position shown in FIG. 2 to the leftmost position (not shown) and vice versa in accordance with the rotational directions of the motor drive shaft 54. The horizontally movable plate 44 carries a dyeing trough 56 (FIG. 2) into which a suitable dyeing liquid agent (not shown in FIGS. 1 and 2) is contained and a decolorization trough 58 into which suitable decolorization liquid agent (not shown in FIGS. 1 and 2) is contained. Both of the troughs 56 and 58 are of a open-topped rectangular box type of the same configuration. The dyeing trough 56 is fixedly mounted on the horizontally movable plate 44 through a bracket 60 fixed to the plate 44. On the other hand, the decolorization trough 58 is swingably supported on the horizontally movable plate 44 by a pair of support members 62 and 64 each one of which is fixed to the horizontally movable plate 44 and each other end of which journals one of shafts 66 and 68 extending outwardly and horizontally from a pair of lugs fixed to the bottom surface of the bottom wall of the decolorization trough 58. The both the shafts 66 and 68 are aligned with each other and disposed at the central portion of the bottom wall of the decolorization trough 58 when seen in FIG. 1. In order to enhance the decolorization effect, the decolorization trough 58 is swung by a swing means 70 which comprises a third motor 72 mounted on the horizonally movable plate 44 through a bracket 74. The swing means also comprises a small disk 76 concentrically fixed to a drive shaft of the motor 72 and a lever 78 one end of which is rotatably connected to the bottom wall of the decolorization trough 58 and the other end of which is also rotatably connected to the small disk 76 at a eccentric position. In FIGS. 1 and 2, the decolorization trough 58 is maintained in the horizontal position where its bottom wall is in parallel with the horizontally movable plate 44. However, when the motor 72 is rotated, the decolorization trough 58 is tilted by means of the small disk 76 and the lever 78 of the swing means 70 with the shafts 66 and 68 being as a fulcrum and then returns to the horizontal position as shown in FIGS. 1 and 2 by the successive rotation of the motor 72. This swinging movement of the decolorization trough 58 will be continued on until the rotation of the motor 72 is stopped.

As shown in FIG. 1, the decolorization trough 58 is shallowed by a partition 80 having recessed portions 80a, 80b and 80c.

Shown in FIG. 1 generally at 82 is a carrier transport mechanism for transporting and holding a specimen carrier 84 of a belt-like form made of, for example, a cellulose acetate paper. The carrier transport mechanism 82 is held at the top of the casing 14 and comprises a support frame 86 having an entrance portion 86a from which the specimen carrier 84 is introduced into the transport mechanism 82, an exit portion 86b from which the specimen carrier 84 is fed out, a top cover wall 86c, and side walls 86d and 86e extending downwardly from the top cover wall 86c. Five pairs of drive rollers 88 – 96 are held between the side walls 86d and 86e so that each drive roller of one pair of the drive rollers can rotate at the position adjacent to one of the side walls 86d and 86e. The length of the span between the drive rollers 90 and 94 is selected so as to be slightly shorter than that of the specimen carrier 84 which is usually used in the blood serum analysis. Each pair of drive rollers are rotated together in the clockwise direction in FIG. 1 through a suitable drive mechanism (not shown) comprising such as an electric motor, gears and/or a chain. Five pairs of driven rollers 98 – 106 are rotatably mounted between the side walls 86d and 86e so as to be driven in cooperation with one pair of the drive rollers 88 – 96. In FIG. 2, only each pair of the drive rollers 92 and the driven rollers 102 are shown for the clarity of the drawing. The specimen carrier 94 is transported from the entrance portion 86a to the exit portion 86b, as will be explained later, through the drive and driven rollers along a path shown by the dotted line 108 in FIG. 1.

A microswitch 110 for controlling the transportation of the specimen carrier 84 is mounted to the inner surface of the top cover wall 86c through a suitable bracket 112 so that its actuating arm 114 extends downwardly beyond the path 108 between the rollers 102 (92) and 104 (94). Another microswitches 116, 118 and 120 with actuating arms 122, 124 and 126, shown in phantom in FIG. 2, are also provided to the casing 14 in order to control the movement of the vertically and horizontally movable plates 34 and 44.

Operation of the dyeing and decolorization apparatus 10 will be described hereinafter.

Before the specimen carrier 84 is introduced into the carrier transport mechanism 82, the vertically movable plate 34 is positioned in its lowermost position and the dyeing trough 56 is positioned below the carrier transport mechanism 82 by operating the first and second electric motors 18 and 50 respectively. The specimen carrier which has been treated in an electrophoretic apparatus (not shown) is fed out from the latter by a suitable transporting means (not shown) to the nips between the drive and driven rollers 88 and 98 through the entrance portion 86a of the carrier transport mechanism 82. If the drive rollers 88 – 96 are rotated simultaneously with the commencement of the operation of the transporting means, the specimen carrier 84 is fed into the carrier transport mechanism 82 by the rollers 88 and 98, and then is advanced toward the right in the carrier transport mechanism 82 by the drive rollers 90 and 92 and the driven rollers 100 and 102 along the path 108 shown in FIG. 1. By the successive advance of the specimen carrier 84 in the righthand direction in FIG. 1, the front end of the specimen carrier 84 abuts on the actuating arm 114 of the microswitch 110, extending downwardly in the position shown in phantom and rotated it counterclockwise. Since the microswitch 110 connected to the motor (not shown) which drives the drive rollers 88 – 96 is switched off when its actuating arm 114 is brought into the position shown by a solid line in FIG. 1 and when the front end of the specimen carrier 84 is nipped by the drive roller 94 and the driven roller 104, the rotation of the drive rollers 90 – 96 are stopped and thus the specimen carrier 84 is held in the carrier transport mechanism 82 in the position shown in FIG. 1 with its front end nipped by the rollers 94 and 104 and its rear end nipped by the rollers 90 and 100.

The first motor 18 is rotated in correspondence with the switch-off operation of the microswitch 110, so that the vertically movable plate 34 is moved upwardly, by the rotated eccentric disk 32, from its lowermost position toward its uppermost position shown in FIGS. 1 and 2. Then the vertically movable plate 34 brought into its uppermost position is held in that position by the eccentric disk 32, because the motor 18 is stopped by the operation of the microswitch 118 which is switched off by a suitable stational member (not shown) fixed to the vertically movable plate so that the stational member is engageable with the actuating arm 124 when the vertically movable plate 34 arrived at its uppermost position. As is described before, since the dyeing trough 56 and the decolorization trough 58 are of the same configuration, the specimen carrier 84 held by the carrier transport mechanism 82 is thoroughly dipped in the dyeing liquid agent contained in the dyeing trough 56 when the vertically movable plate 34 is held in its uppermost position. Though the relation between the dyeing trough 56 and the specimen carrier 84 when the vertically movable plate 34 is in its uppermost position is not shown in the drawings, this relation is the same as one between the decolorization trough 58 and the specimen carrier 84 shown in FIGS. 1 and 2. In this manner, the specimen carrier 84 and the specimens i.e. the blood serums applied thereto are dyed together by the dyeing liquid agent in the dyeing trough 56. After the dyeing process for the specimen carrier 84 and the specimens applied thereto has been sufficiently carried out, the first motor 18 is again rotated by the operation of, for example, a timer (not shown) so that the vertically movable plate 34 is moved downwardly to its lowermost position. When the vertically movable plate 34 is brought into its lowermost position, the rotation of the motor 18 is stopped by the operation of the microswitch 116 which is also connected to the motor 18 and which is switched off by the lower surface of the vertically movable plate 34 engageable, at its lowermost position, with the actuating arm 122 of the microswitch 116. Therefore, the vertically movable plate 34 is again held in its lowermost position and the dyeing process for the specimen carrier 84 and the blood serum applied thereto is terminated.

Then, the second motor 50 is rotated in correspondence to the vertically movable plate 34 being brought into its lowermost position, in order to move the horizontally movable plate 44 through the pinion 52 and the rack 48 to the position where the dyeing trough 56 was previously placed i.e. the place below the carrier transport mechanism 82. When the decolorization trough 58 has arrived at the position described above, the rotation of the second motor 50 is stopped by the operation of a microswitch (not shown) as in the same manner as in the cases of the microswitches 116 and 118, and thus the horizontally movable plate 44 is held in the position. At the same time, the first motor 18 is again rotated so that the vertically movable plate 34 is moved from its lowermost position to its uppermost position shown in FIGS. 1 and 2. Then, the vertically movable plate 34 is held again in its uppermost position as in the same manner as described before. Therefore, the specimen carrier 84 held in the carrier transport mechanism 82 is thoroughly dipped into the decolorization liquid agent contained in the decolorization trough 58 as shown in FIGS. 1 and 2 and the decolorization process for the specimen carrier 84 is carried out. In order to enhance the decolorization effect, the third motor 72 is rotated correspondingly to the vertically movable plate 34 having arrived in its uppermost position so that the decolorization trough 58 is swung by the swing means 70 with a pair of the shafts 66 and 68 being as a fulcrum.

The decolorization liquid agent which has been polluted, as the decolorization process progresses, by the dyeing or colorization matter removed from the specimen carrier 84 is discharged by a suitable discharging means from the decolorization trough 58 and the fresh liquid agent for the decolorization is refilled in the decolorization trough 58. This discharging and refilling of the decolorization liquid agent is repeated for several times during the decolorization process for the specimen carrier 84. By the swinging movement of the decolorization trough 58 and by the repetition of the discharging and refilling of the decolorization liquid agent, the specimen carrier 84 is sufficiently, decolorized or cleared except for the portions of the blood serums applied thereto after a certain period of time. The first motor 18 is again rotated at this time by the operation of a timer (not shown) so that the vertically movable plate 34 is moved to its lowermost position together with the decolorization trough 58, and the decoloriation process for the specimen carrier is terminated. Then the vertically movable plate 34 is held in its lowermost position since the rotation of the first motor 18 is stopped by the operation of the microswitch 116. Corresponding to the completion of the decolorization process the drive roller 90 – 94 are again rotated in the clockwise direction, so that the specimen carrier 84 subjected to the dyeing and decolorization processes is fed out through the exit portion 86b to the place where the next process such as a drying process may be carried out. At the same time when the specimen carrier 84 is being transported along the path 108 or when the transportation of the specimen carrier 84 is terminated, the second motor 50 is again rotated so as to return the horizontally movable plate 44 to the original position where the colorization trough 56 is placed below the carrier transport mechanism 82. When the horizontally movable plate 44 is returned to the above mentioned position, the rotation of the second motor 50 is stopped by the operation of the microswitch 120 and the motor for driving the drive rollers 88 – 96 is also stopped simultaneously. Thus, all of the mechanisms of the dyeing and decolorization apparatus 10 are prepared for the next dyeing and decolorization operations.

Figure 3:
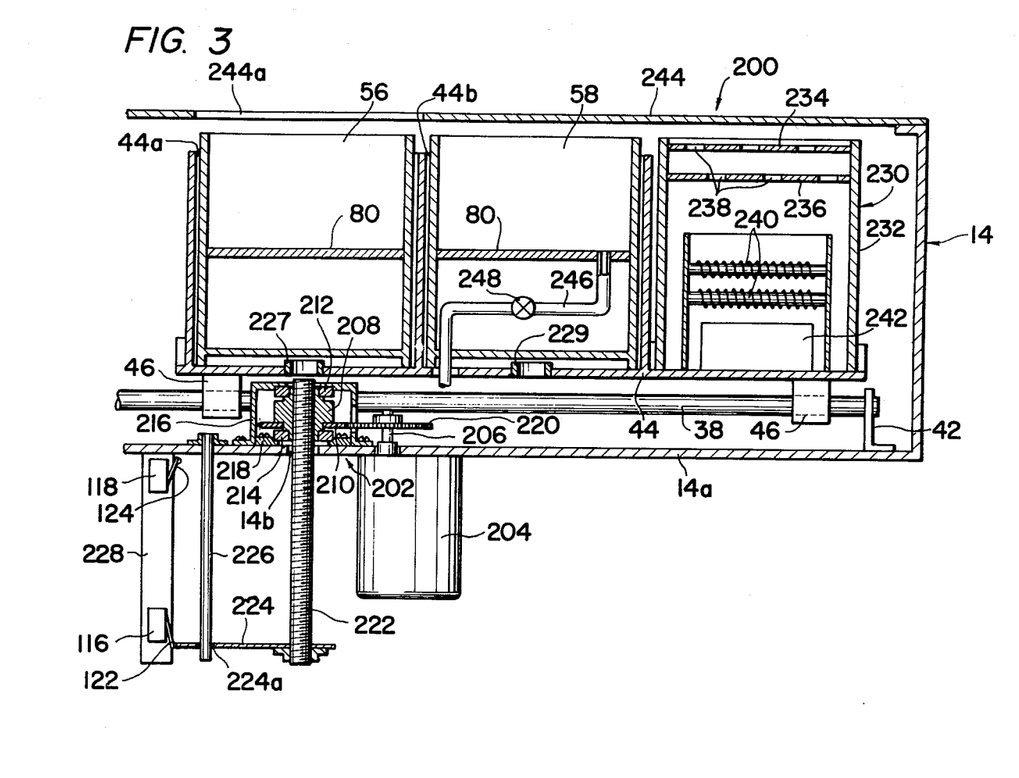
FIG. 3 shows a fragmentary sectional side elevational veiw of another embodiment of a dyeing and decolorization apparatus in accordance with the present invention.

Another embodiment of a dyeing and decolorization apparatus in accordance with the present invention is shown in FIG. 3. This apparatus 200 includes a elevating mechanism for elevating independently the dyeing trough 56 and decolorization trough 58 instead of vertically moving them together as the embodiment shown in FIGS. 1 and 2. The elevating mechanism 202 comprises an electric motor 204 fixed to the bottom wall 14a of the casing 14 in the manner that a drive shaft 206 thereof extends uprightly through the bottom wall 14a. On the bottom wall 14a near the motor drive shaft 206, a nut 208 integrally provided with a gear 210 is rotatably supported, with its central axis being parallel with the motor drive shaft 206, by a pair of bearing means 212 and 214 which are respectively held by a gear housing 216 and an annular mount 218 fixed to the bottom wall 14a of the casing 14. A gear 220 fixed to the drive shaft 206 of the motor 204 is in meshing engagement with the gear 210 of the nut 208 through a window of the gear housing so that the rotation of the motor 204 is transmitted to the nut 208. A pushing rod or bolt 222 provided with its lower end a switch actuating lever 224 is screwed into the nut 208 throuh a hole 14b of the casing 14. The swich actuating lever 224 extending in the leftward direction in FIG. 3 is provided with a small hole 224a adjacent to its free end. A guide post 226 fixed to the bottom wall 14a of the casing 14 and extending downwardly in parallel with the bolt 222 is loosely inserted into the small hole 224a of the switch actuating lever 224 so that the rotation of the bolt 222 will be prevented. Therefore, if the motor 204 is rotated the bolt 222 is advanced upwardly or downwardly depending on the rotational direction of the motor drive shaft 206. The free end of the switch actuating lever 224 is engageable with the actuator arms 122 and 124 of the microswitches 116 and 118 to switch over them when the switch actuating lever 224 i.e. the bolt 222 is positioned in its lowermost position shown in FIG. 3 and in its uppermost position respectively, which microswitches 116 and 118 are respectively mounted to a support member 228 fixed to the bottom wall 14a of the casing 14.

In this embodiment, the horizontally movable plate 44 is provided with chambers 44a and 44b for loosely receiving the dyeing trough 56 and the decolorization trough 58. The horizontally movable plate 44 is also provided with holes at the central portions of the chambers 44a and 44b, to which bushing 227 and 229 are fixedly inserted. The inner diameter of each bushing is selected larger than that of the bolt 222 so that the bolt 222 can pass therethrough as described in detail later. A dryer means 230 is mounted on the horizontally movable plate 44 in series to the chambers 44a and 44b, which dryer means comprises a cover casing 232, top cover plates 234 and 236 provided with a plurality of apertures 238, an electric heater 240 and a blower means 242, so that heated air will be blown upwardly through the apertures 238 of the top cover plates 234 and 236. The horizontally movable plate 44 is slidably supported on the guide rod 38 and on another guide rod (not shown) and is horizontally moved by a rack and pinion mechanism (not shown) in the same manner as in the embodiment of FIGS. 1 and 2. Since the position of the bolt 222 is selected so that its axis is intersect with the travelling path of each center of the bushes 227 and 229, the horizontally movable plate 44 can be stopped at the positions where the bushes 227 and 229 are respectively aligned with the bolt 222. A top cover 244 with a rectangular opening 244a is fixed on the top of the casing 14. The opening 244a is formed at the position above the bolt 222 so as to permit the dyeing trough 56 or decolorization trough 58 to pass through it when they pushed upwardly by the bolt 222 as will be described later in detail. In order to discharge the polluted decolorization liquid agent, a conduit 246 is connected to the partition 80 of the decolorization trough 58. Discharging of the polluted decolorization liquid agent is carried out by the manipulation of a valve 248 disposed in the conduit 246. A carrier transport mechanism (not shown) similar to one shown in FIGS. 1 and 2 at 82 is mounted to the casing 14 so that it locates above the opening 244a of the top cover 244. In this embodiment, the dyeing trough 56 and decolorization trough 58 are successively placed in the position below the opening 244a of the top cover 244, where the bushing 227 and 229 are respectively aligned with the bolt 222, by the horizontal movement of the horizontally movable plate 44 and either one of the troughs 56 or 58 placed below the opening 244 is moved from its lowermost position shown in FIG. 3 to its uppermost position where the speciment carried held in the carrier transport mechanism is thoroughly dipped into the liquid agent contained in the trough, when the bolt 222 is advanced upwardly through either one of the bushings 227 or 229 from its lowermost position shown in FIG. 3 to its uppermost position by the motor 204. Since the bolt 222 is advanced downwardly by reversing the rotational direction of the motor 204, the dyeing trough 56 or decolorization trough 58 held in its uppermost position by the bolt 222 is returned to its lowermost position by the gravity when the bolt is returned to its lowermost position. After the dyeing and decolorization processes are successively carried out, the specimen carrier is held in the carrier transport mechanism as it is for predetermined periods of time so as to be subjected to the drying process by the dryer means 230 which will be placed to the position below the opening 244a subsequent to the termination of the decolorization process.

The dyeing and decolorization apparatus 200 shown in FIG. 3 can be arranged compact and light weighted in comparison with the apparatus shown in FIGS. 1 and 2, since it is not necessary to move together the dyeing and decolorization troughs.

Figure 4:
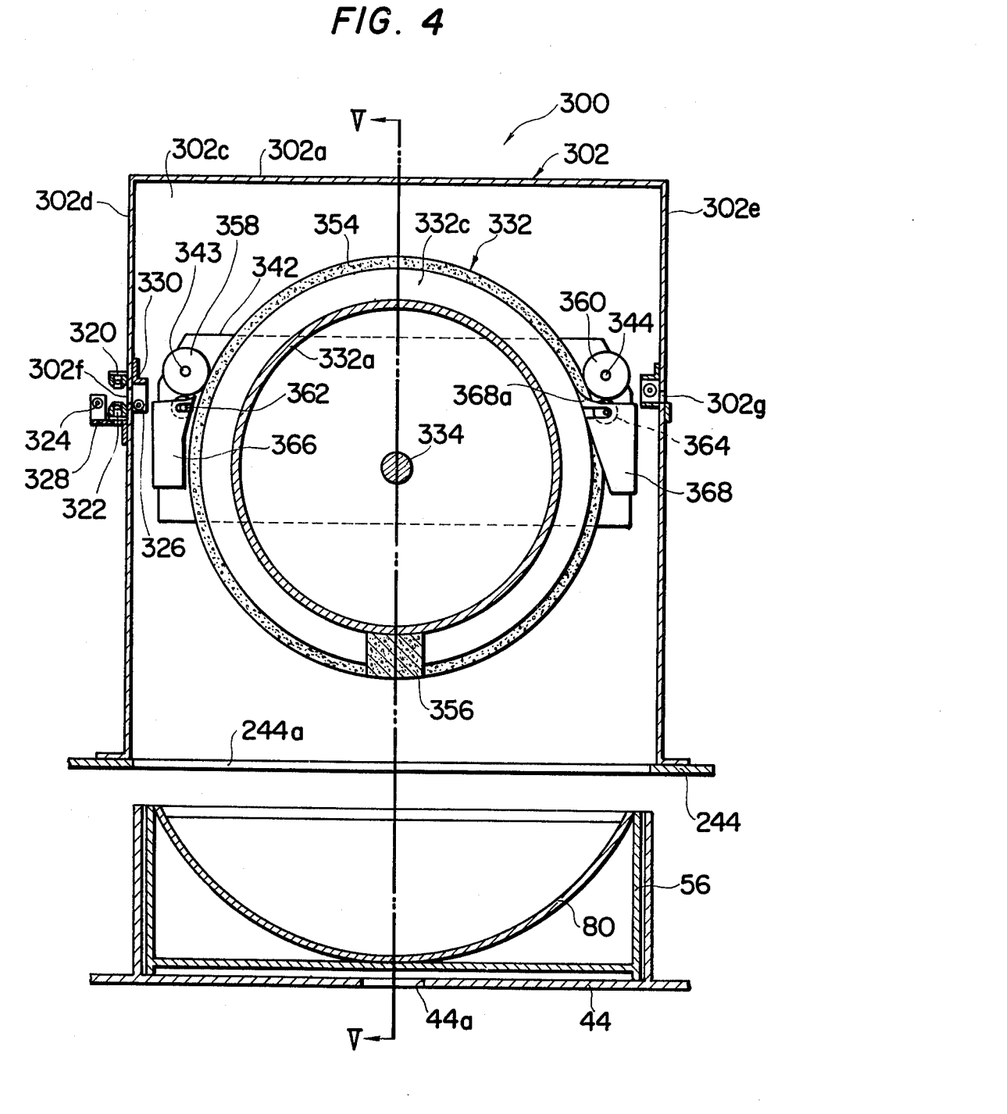
FIG. 4 shows a sectional side elevational view of another embodiment of a carrier transport mechanism in accordance with the present invention for use in the dyeing and decolorization apparatus of the invention.
Figure 5:
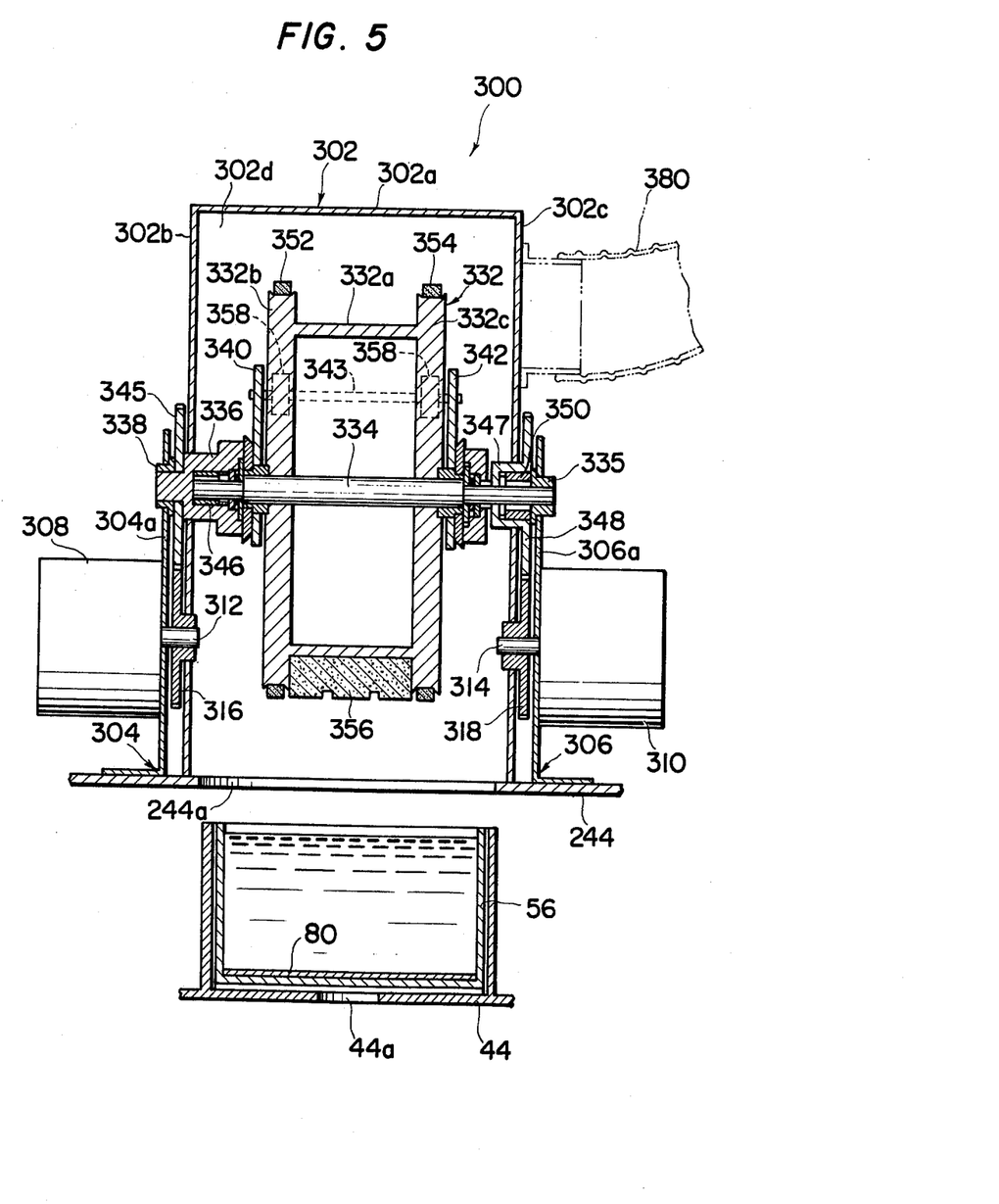
FIG. 5 shows a sectional front elevational view taken along the line V—V of FIG. 4.
Figure 6:
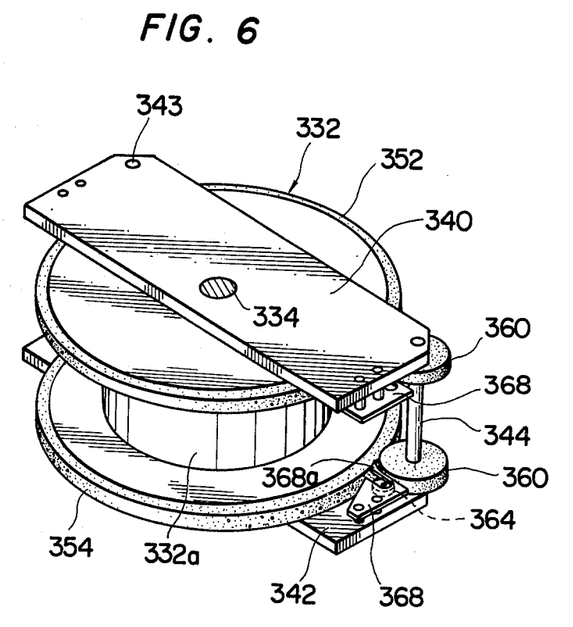
FIG. 6 shows a perspective view of a drum used in the carrier transport mechanism shown in FIGS. 4 and 5.

FIGS. 4 through 6 show another type of the carrier transport mechanism 300 which may be adapted to both of the embodiments of the invention shown in FIGS. 1 and 2, and FIG. 3. The carrier transport mechanism 300 includes a open-bottomed casing 302 having a top wall 302a, side walls 302b and 302c, a front wall 302d and a rear wall 302e. The casing 302 is fixedly mounted, for example, on the top cover 244 of the dyeing and decolorization apparatus 200 shown in FIG. 3, with the bottom opening thereof aligned with the opening 244a of the top cover 244. The casing 302 is provided with a entrance window 302f for introducing the specimen carrier (not shown) in to the transport mechanism 300 and a exit window 302g for feed out the specimen carrier from the transport mechanism 300.

Outside the casing 302, a pair of L-shaped support members 304 and 306 (FIG. 5) are oppositely fixed on the top cover 244 at the positons adjacent to the side walls 302b and 302c with their upwardly extending portions 304a and 306b being parallel with the side walls 302b and 302c respectively. Electric motors 308 and 310 are secured to the upwardly extending portion of the support members 304 and 306 in the manner that their drive shafts 312 and 314 to which gears 316 and 318 are concentrically fixed extend inwardly through the upwardly extending portions 304a and 306a.

Back to FIG. 4, a light source 320 such as a light emission diode and a light reception element 322 such as a photoelectric or photoconductive element are fixed to the outer surface of the front wall 302d of the casing 302 at the positions immediately above and below the entrance window 302f. These light source 320 and light reception element 322 are used to detect the arrival of the specimen carrier to be fed into the carrier transport mechanism 300. In order to introduce the specimen carrier smoothly, a pair of guide rollers 324 and 326 are also disposed near the entrance window 302f by means of brackets 328 and 330 fixed to the outer and inner surfaces of the front wall 302d. Inside the casing 302, a drum 332 is rotatably supported by the support members 304 and 306 through its center shaft 344 one end portion of which extends outwardly through an aperture formed in the side wall 302c into a bearing means 335 fixed to the support member 306 for the smooth rotation of the shaft 334 and the other end portion of which is inserted in a bore of a geared member 336 that is rotatably supported by a bearing means 338 fixed to the support member 304. A pair of support plates 340 and 342 connected with each other by roller shafts 343 and 344 are rotatably mounted on the center shaft 334 so as to interpose the drum 332 between them. The inner end of the geared member 336 is fixed to the support plate 340 so that geared member 336 can rotate together with a pair of the support plates 340 and 342. The geared member 336 is provided with a gear 345 which can be in meshing engagement with the gear 316. In the bore of the geared member 336, a one-way clutch 346 is disposed between the inner surface of the bore and the end portion of the center shaft 334 so that the geared member 336 and the center shaft 334 are coupled only when the geared member 336 is rotated in the counterclockwise direction when seen from the left in FIG. 5. Another geared member 347 is loosely mounted on the opposite end portion of the center shaft 334 so that its gear 348 is in meshing engagement with the gear 318. A one-way clutch 350 similar to one shown at 346 is disposed between the geared member 347 and the center shaft 334 so that the rotation of the motor 310 may be transmitted to the center shaft 334 only when the motor rotates the geared member 347 in the clockwise direction when seen from the right in FIG. 5.

The drum 332 per se consists of a cylindrical body portion 332a and a pair of disk-like flange portions 332b and 332c. The periphery of both flange portions 332b and 332c are surrounded by annular sponge belts 352 and 354. In a part of a recess formed by the periphery of the body portion 332a and both flange portions 332b and 332c, a catch member of generally rectangular parallelepiped shape is fixedly inserted with its outer surface being flush with the periphery of the sponge belts 352 and 354. The catch member is also made of sponge and serves to catch the front end portion of the specimen carrier. Two pair of rollers 358 and 360 are rotatably mounted on th roller shafts 343 and 344 so that they engages with the pheripheries of the annular sponge belts 352 and 354. The support plates 340 and 342 are also provided with two pairs of small rollers 362 and 364 each periphery of which is engaged with the periphery of each of the rollers 358 and 360. Two pairs of guide plates 366 and 368 are fixed to the support plates 340 and 342 at the positions adjacent to the rollers 358 and 360. Each of the guide plates 368 is provided with a nail portion 368a which extends ineardly along the inner surface of each sponge belt.

Operation of this carrier transport mechanism 300 is as follows.

Before the specimen carrier (not shown) is introduced to the entrance window 302f of the casing 302 by another suitable transport means (not shown), all mechanisms are placed into the position shown in FIGs. 4 and 5. When the specimen carrier is fed between the light source 320 and the light reception element 322, the arrival of the specimen carrier is detected by the variation of the output gain of the light reception elements 322 and simultaneously the motor 310 is rotated so that the drum is rotated in the clockwise direction in FIG. 4. Since the left side end portion of the center shaft 334 in FIG. 5 is slipped with respect to the one-way clutch 346, the support plates 340 and 342 are held in the horizontal position shown in FIGS. 4 and 5. The front end portion of the specimen carrier is then nipped by the rollers 358 and 362 and fed toward the periphery of the sponge belts 352 and 354. Since the catch member 356 is brought into the position near the nips between the rollers 358 and 362 by the rotation of the drum 352 when the front end portion of the specimen carrier comes out from the nip, the front end portion of the specimen carrier is caught by the peripheral surface of the catch member 356 due to the strong friction therebetween. Thus the specimen carrier is swathed around the drum 332 along the periphery of the sponge belts 352 and 354 as the drum rotates. When the front end portion of the specimen carrier caught by the catch member 356 arrives at the position near the roller 360, the front end portion of the specimen carrier is torn off from the catch member 356 by the nail portions 368a of the guide plates 368 and guided to the nip between the rollers 360 and 364 as the rotation of the drum proceeds. Since the length of the periphery of the sponge belt 352 and 354 between the portion adjacent to the roller 358 and the portion adjacent to the roller 360 is selected somewhat shorter than the length of the specimen carrier usually used for the purpose of the blood serum analysis, the rear end portion of the specimen carrier is being nipped by the roller 358 and 362 when the front end portion thereof is nipped by the roller 360 and 364. Therefore, if the motor 310 is stopped at this time, the specimen carrier is held on the sponge belts 352 and 354 of the drum 332 with its front and rear end portions nipped by the rollers 360 and 364 and the rollers 358 and 362. Actually, the motor 310 is stopped by, for example, a timer (not shown) when the front end portion of the specimen carrier is nipped by the rollers 360 and 364, and simultaneously the motor 308 is rotated so that the geared member 336 is rotated in the counterclockwise direction when seen from the left in FIG. 5. Thus, in this case, a pair of the support plates 340 and 342 and the drum 332 are rotated together in the clockwise direction in FIG. 4. Then, the motor 308 is stopped by the operation of the timer when the specimen carrier swathed around the drum 332 with its both end portion nipped by the rollers 358, 362, 360 and 364 is brought into the position where the longitudinal center portion of the specimen carrier is being the lowermost position. The dyeing trough 56 is then pushed up from its lowermost position shown in FIGS. 4 and 6 through opening 244a of the top cover 244 by means of an elevating mechanism (not shown) similar to the one shown in FIG. 3 up to the position where the specimen carrier held around the lower periphery of the drum 332 is thoroughly dipped into the dyeing liquid agent contained in the dyeing trough 56. After the predetermined periods of time, the dyeing trough 56 is lowered and then the decolorization trough (not shown) is pushed up for the decolorization process through the opening 244a as in the same manner as described in connection with the embodiment shown in FIG. 3. Subsequent to the completion of the dyeing and decolorization processes, the motor 308 is again rotated until the support plates 340 and 342 are returned together with the drum 332 to the position shown in FIGS. 4 and 5. Then the motor 310 is rotated again to rotate the drum in the clockwise direction in FIG. 4 to feed out the specimen carrier through the exit window 302g of the casing 302.

In the dyeing and decolorization apparatus 300 shown in FIGS. 4 and 5, it is preferable to introduce heated air into the casing 302 from a dryer means (not shown) similar to the one shown in FIG. 3 by using a duct 380 shown in phantom in FIG. 5, after the decolorization process for the specimen carrier has been carried out.

What is claimed is:

1. An apparatus for dyeing and decolorizing a predetermined length of a specimen carrier having a front and rear end of a belt-like shape, carrying a plurality of specimens such as blood serums which have been treated by an electrophoretic apparatus comprising a carrier transport mechanism for receiving and holding the specimen carrier therein during dyeing and decolorization processes for the specimen carrier and for transporting the specimen carrier out of the dyeing and decolorization apparatus after the completion of said processes, a dyeing trough containing a dyeing liquid agent and supported movably with respect to the carrier transport mechanism, a decolorization trough containing a decolorization liquid agent and supported movably with respect to the carrier transport mechanism, a first drive means for moving said dyeing and decolorization troughs in a vertical direction and a second drive means for moving said dyeing and decolorization troughs in a horizontal direction, said carrier transport mechanism comprising a drum having a center shaft, a pair of support plates rotatably mounted on said shaft at a position adjacent both side walls of the drum so that said drum lies therebetween, two pairs of rollers rotatably supported between the support plates with the pairs being spaced apart a given distance along the periphery of the drum, said distance being less than the length of the specimen carrier so that the peripheries of each roller engage the periphery of the drum, a third drive means for rotating only the drum and a fourth drive means for rotating the drum and the support plates together so that after said third drive means rotates said drum so that the specimen carrier is fed onto the carrier transport mechanism with both ends held between said two pairs of rollers and said drum, said drum and said plates are rotated together by said fourth drive means only until the specimen carrier is positioned so that the longitudinal center of the specimen carrier is at its lower most position in a treating position thereby allowing thorough treatment in each of said dyeing and decolorization troughs when they are subsequently moved into treating positions with respect to the specimen carrier.

2. An apparatus for dyeing and decolorizing a specimen carrier according to claim 1, wherein the dyeing and decolorization troughs are mounted on a horizontally movable plate which is supported on a vertically movable plate, and the dyeing and decolorization troughs are moved, with respect to the specimen carrier held in the carrier transport mechanism, by the first and second drive mechanisms through the verically and horizontally movable plates.

3. An apparatus for dyeing and decolorizing a specimen carrier according to claim 1, wherein said first drive mechanisms is a pushing rod which is disposed below the carrier transport mechanism so that it can push up each of the dyeing and decolorization troughs independently and alternately toward the carrier transport mechanism until the specimen carrier held in the carrier transport mechannism is thoroughly dipped into the liquid agent contained in the pushed-up trough.

4. A carrier transport mechanism according to claim 1, wherein at least a pair of sponge belts are fixed around the periphery of the drum so that the specimen carrier is swathed on the periphery of the sponge belts due to the friction therebetween.

5. A carrier transport mechanism according to claim 1, wherein a catch member made of sponge is fixed to a part of the drum with its peripheral surface being flush with the peripheries of the sponge belts so that the catch member catch the front end portion of the specimen carrier by the friction therebetween.

6. The dyeing and decolorizing apparatus as in claim 1 further comprising a housing means for enclosing at least part of said apparatus including said carrier transport mechanism having openings on opposite sides of said housing means respectively defining an entrance to and an exit from said housing means to allow for passage of predetermined lengths of said specimen carrier into and out of said housing means, a photoelectric eye positioned adjacent the entrance to said housing means for sensing the presence of said specimen carrier.

7. Apparatus for dyeing and decoloring a specimen carrier of a belt-like shape having a plurality of electrophoretically treated specimens thereon comprising:

housing means for enclosing at least part of said apparatus having on opposite sides of said housing means respectively defining an entrance to and an exit from said housing means to allow for passage of predetermined lengths of said specimen carrier into and out of said housing means;

carrier transport means positioned within said housing means so as to cooperate with the entrance and exit thereof for receiving predetermined lengths of said specimen carrier, for positioning the predetermined lengths of said specimen carrier, for processing and for feeding the predetermined lengths of specimen carrier from said housing means following processing:

said carrier transport means including holding means for holding each end of the predetermined length of said specimen carrier in a predetermined position on said carrier transport means, a first transport drive means for driving said carrier transport means for receiving the predetermined lengths of said specimen carrier from the entrance to said housing means and feeding the specimen carrier to said holding means and for feeding the predetermined length of said specimen carrier from said housing means and a second transport drive means for positioning said carrier transport means together with the predetermined length of said specimen carrier in a processing position;

treating means for treating the predetermined length of said specimen carrier when said carrier transport means is held in its processing position, said treating means including dyeing means for dyeing the predetermined length of said specimen carrier and decolorization means for decolorizing the predetermined length of said specimen carrier;

treating drive means for successively moving said dyeing means and said decolorization means into a treating position with respect to the predetermined length of said specimen carrier positioned on said carrier transport means so that the specimen carrier is thoroughly treated by both of said dyeing and decolorization means; and actuating means for sensing the presence of said specimen carrier at the entrance of said housing means and for actuating said apparatus in response to the sensing of said specimen carrier.

8. The dyeing and decolorizing apparatus as in claim 7 wherein said actuating means includes a photoelectric eye positioned adjacent the entrance to said housing means for sensing the presence of said specimen carrier and wherein said carrier transport means further includes a drum having a center shaft, support plate means rotatably mounted on the center shaft of said drum for supporting said holding means, said holding means including first and second pressure roller means rotatably supported on said support plate means for cooperating with the periphery of said drum for engaging the predetermined length of said specimen carrier, said first and second roller means being spaced apart a given distance about the periphery of said drum, said distance being less than the predetermined length of said specimen carrier so that when said specimen carrier is fed onto said carrier transport means said holding means will be positioned so as to engage respectively the front and rear ends of the predetermined length of said specimen carrier said first transport drive means being drivingly correctable to said shaft for rotating only said drum, said second transport drive means being drivingly correctable to said shaft and said support plate means for rotating said drum and said support plate means together.

9. The dyeing and decolorization apparatus as set forth in claim 7 wherein said treating drive means includes a first drive means for moving said dyeing and decolorization means successively into alignment with said carrier transport means and a second drive means for moving said dyeing and decolorization means successively into and out of a treatment position with respect to said carrier transport means whereby after the predetermined length of said specimen carrier has been positioned by said carrier transport means in its processing position said specimen carrier can be successively dyed and decolorized.

10. Apparatus for dyeing and decoloring as in claim 7 further including swing means for swinging said decolorization means.

* * * * *